(12) United States Patent
Righi et al.

(10) Patent No.: US 12,048,652 B2
(45) Date of Patent: Jul. 30, 2024

(54) PROTECTIVE EYE MASK FOR THE PRACTICE OF WINTER SPORTS

(71) Applicant: OUT OF S.R.L., Brescia (IT)

(72) Inventors: Federico Righi, Brescia (IT); Roberto Righi, Brescia (IT)

(73) Assignee: OUT OF S.R.L., Brescia (IT)

( * ) Notice: Subject to any disclaimer, the term of this patent is extended or adjusted under 35 U.S.C. 154(b) by 116 days.

(21) Appl. No.: 17/758,319

(22) PCT Filed: Jan. 12, 2021

(86) PCT No.: PCT/IB2021/050181
§ 371 (c)(1),
(2) Date: Jul. 1, 2022

(87) PCT Pub. No.: WO2021/144684
PCT Pub. Date: Jul. 22, 2021

(65) Prior Publication Data
US 2023/0029086 A1   Jan. 26, 2023

(30) Foreign Application Priority Data
Jan. 14, 2020   (IT) .......................... 102020000000526

(51) Int. Cl.
*A61F 9/02* (2006.01)
*G02F 1/13* (2006.01)

(52) U.S. Cl.
CPC .............. *A61F 9/029* (2013.01); *A61F 9/023* (2013.01); *G02F 1/13* (2013.01)

(58) Field of Classification Search
None
See application file for complete search history.

(56) References Cited

U.S. PATENT DOCUMENTS

| 5,172,256 A | 12/1992 | Sethofer et al. |
| 6,239,778 B1 | 5/2001 | Palffy-Muhoray et al. |
| 7,567,306 B2 | 7/2009 | Park et al. |
| 2011/0283431 A1* | 11/2011 | Miller, IV .............. G02C 7/101 2/10 |
| 2014/0092328 A1* | 4/2014 | Werthmuller ........... A61F 9/023 349/14 |
| 2018/0045981 A1 | 2/2018 | Cornelius et al. |

FOREIGN PATENT DOCUMENTS

EP          0298983 A1    1/1989

OTHER PUBLICATIONS

International Search Report and Written Opinion for corresponding PCT/IB2021/050181 mailed Apr. 30, 2021, 10 pages.

* cited by examiner

*Primary Examiner* — Ashok Patel
(74) *Attorney, Agent, or Firm* — Armstrong Teasdale LLP

(57) ABSTRACT

A protective eye mask for practicing winter sports and in particular alpine skiing is provided. The protective eye mask is provided with an electrically powered lyquid crystal (LC) lens having at least one LC layer made of guest-host (GH) type liquid crystals.

11 Claims, 4 Drawing Sheets

PROTECTIVE EYE MASK FOR THE PRACTICE OF WINTER SPORTS

CROSS-REFERENCE TO RELATED APPLICATION

This application is a National Stage Application of International Patent Application No. PCT/IB2021/050181, having an International Filing Date of Jan. 12, 2021, which claims priority to Italian Application No. 102020000000526 filed Jan. 14, 2020, the entire contents of which are incorporated by reference herein.

FIELD OF THE INVENTION

The present invention relates to a protective eye mask for the practice of winter sports, and in particular alpine skiing.

BACKGROUND OF THE INVENTION

As is known, alpine skiing is a winter sport which consists in descending down a mountain slope by sliding on the snow with a pair of skis.

In order to protect the eyes and improve visibility, skiers usually wear a ski mask provided with lenses which, in addition to protecting the eyes, cover much of the upper part of the face. The lenses are variously colored: those which are darkest are used for mainly sunny days, while the lighter ones are used for days with poor visibility.

However, during a descent, some sections of the slope may be sunny, while other sections may be in the shade or cross wooded areas; furthermore, it frequently occurs that during a skiing session, which can last a few hours, a sunny day becomes cloudy or vice versa.

In order to meet the needs of skiers, ski masks with color-changing lenses have been designed, capable of independently changing the color thereof according to the amount of light in the environment.

For example, some known solutions are provided with photochromic lenses capable of changing color when exposed to sunlight. However, the color change of such lenses is extremely slow, and they are not effectively usable in the descents of alpine skiing when sunny areas and shaded areas follow one another very quickly with the skier's descending speed.

Masks are also known which are provided with electrochromic lenses, which change color when subjected to an electrical voltage. However, such masks provide for the lenses to be electrically powered with a rather high power, which implies the use of batteries. However, such batteries are bulky, too heavy for a comfortable use of the mask, and obviously need to be recharged. Lastly, the energy consumption is so high that the color change of the lenses, carried out automatically or controlled manually by the skier, can only occur a small number of times (about twenty) before the batteries must be recharged.

Certain masks with lenses provided with a liquid crystal layer (LC) powered by batteries are also known. Such a solution is described, for example, in EP-A1-298983. As mentioned, the use of batteries makes such a solution uncomfortable.

SUMMARY OF THE INVENTION

It is the object of the present invention to provide a protective eye mask for the practice of winter sports, and in particular for alpine skiing, which overcomes the above-mentioned drawbacks and meets the field needs.

Such an object is achieved by a protective mask as described and claimed herein. Advantageous embodiments of the present invention are also described.

BRIEF DESCRIPTION OF THE FIGURES

The features and advantages of the protective mask according to the present invention will become apparent from the following description, given by way of non-limiting example, according to the accompanying drawings, in which.

DETAILED DESCRIPTION

Figure 1:
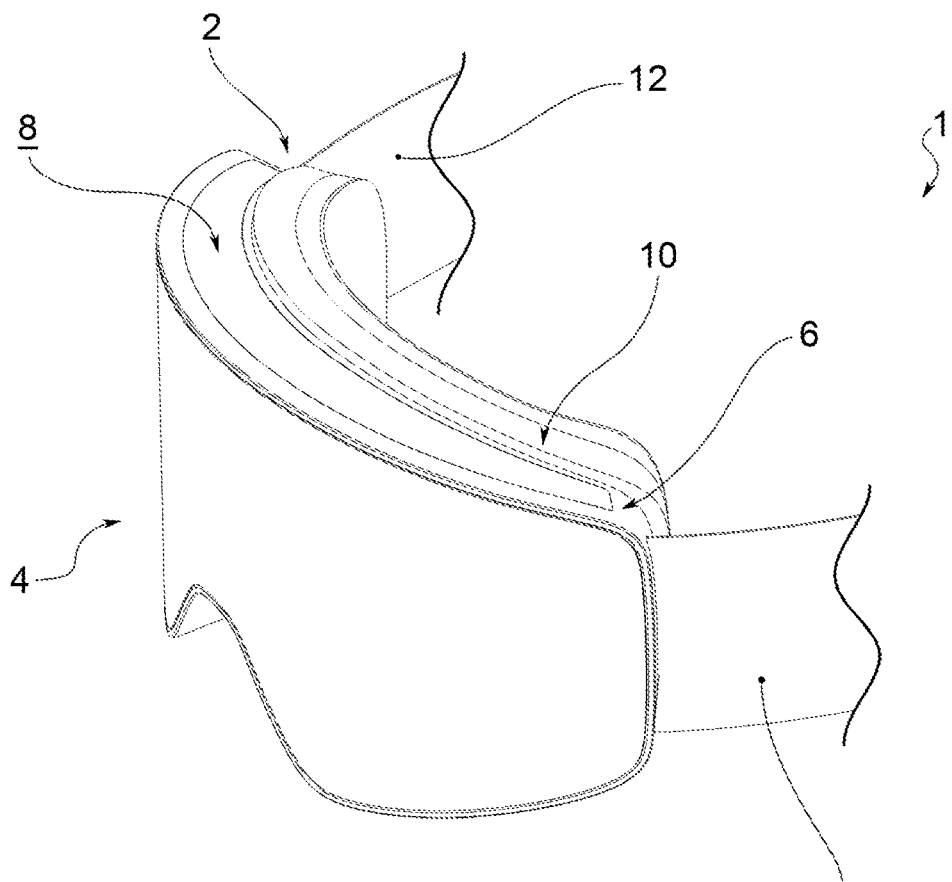
FIG. 1 shows a protective eye mask according to an embodiment of the present invention.
Figure 2:
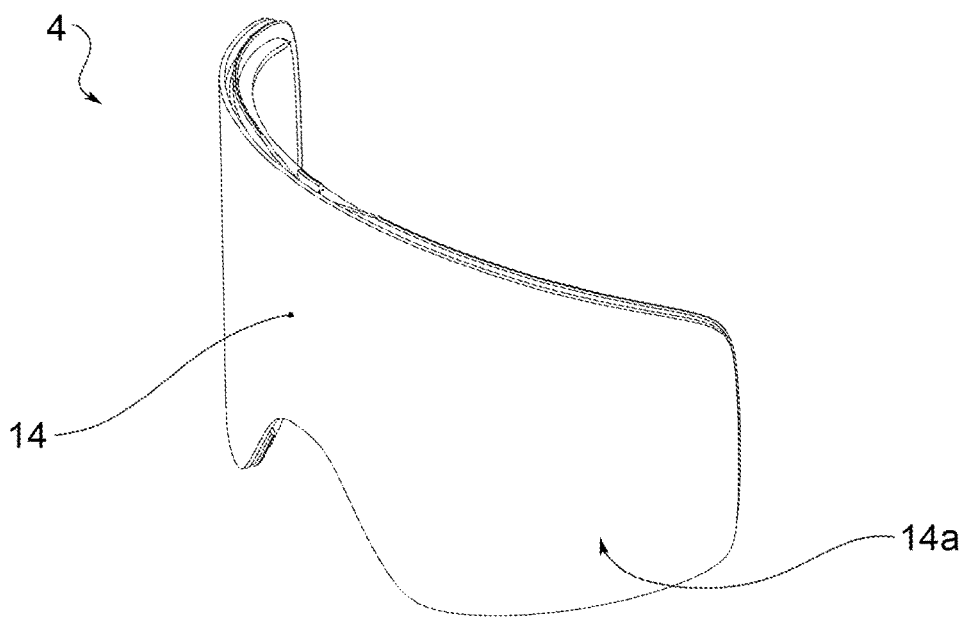
FIG. 2 depicts a lens assembly of the protective mask in FIG. 1.
Figure 3:
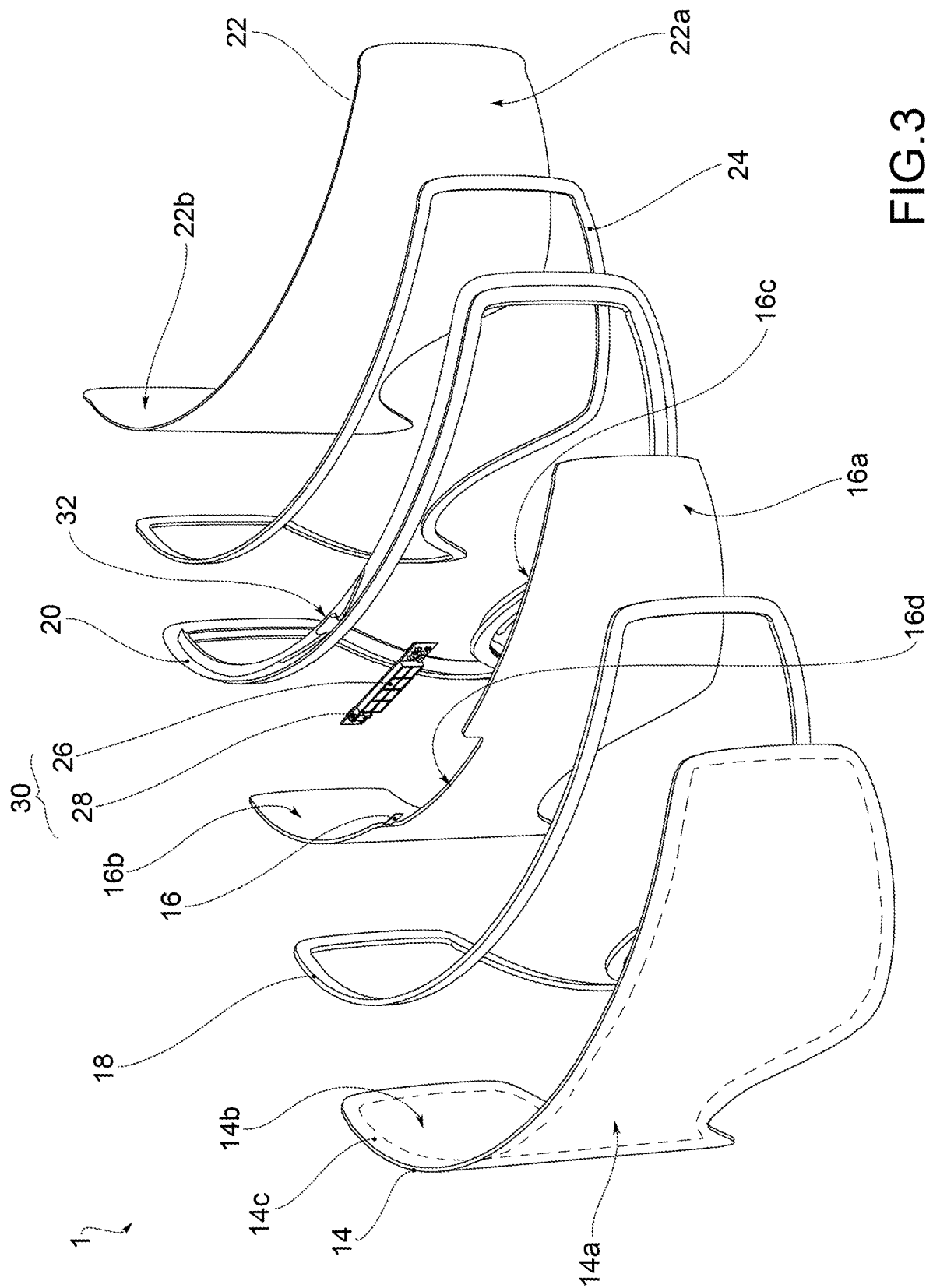
FIG. 3 shows the lens assembly in FIG. 2, with separate parts.
Figure 4:
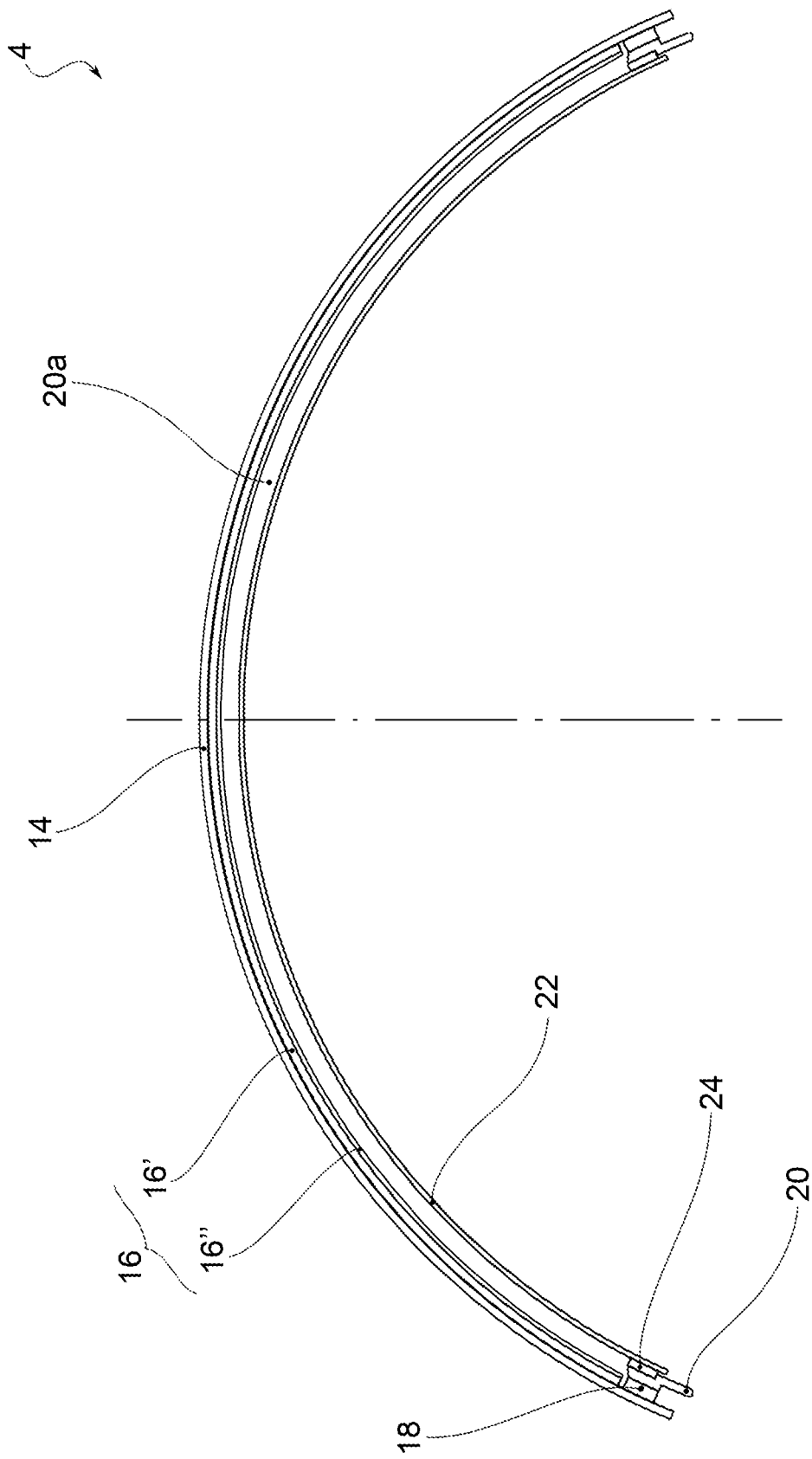
FIG. 4 shows the lens assembly in FIG. 2, according to a cross-sectional view.

With reference to the figures of the accompanying drawings, reference numeral 1 indicates as a whole a protective face mask for winter sports, in particular for alpine skiing, according to an embodiment of the present invention.

The mask 1 comprises a support assembly 2 and a lens assembly 4, applied to the support assembly 2.

The support assembly 2 comprises a support 6, generally made in a single piece of polymer material, which is suitable for the application of the lens assembly 4, for example by means of an interlocking system.

Furthermore, the support 6 preferably has ventilation windows 8 for the air to enter into the mask; usually, said ventilation windows are obtained at the top and/or at the bottom.

The support assembly 2 further comprises contact portions 10, usually made of sponge or other soft material, located peripherally to the support 6, internally with respect to the lens assembly 4, intended to contact and adhere to the face to limit the entry of air currents towards the eyes.

Preferably, the mask 1 lastly comprises an elastic band 12, usually applied to the sides of the support 6, for holding the mask to the face.

According to a preferred embodiment, the lens assembly 4 comprises an outer lens 14, usually made of polycarbonate, having an outer surface 14a and an inner surface 14b.

The lens assembly 4 further comprises a liquid crystal lens 16 (hereinafter LC lens), provided with an outer face 16a, facing the outer lens 14, and an inner face 16b.

The LC lens 16 is applied to the outer lens 14, and in particular to the inner surface 14b thereof, preferably by means of lamination. According to a preferred embodiment, the shape of the LC lens 16 is contained in the shape of the outer lens 14, so that an adhesion zone 14c is peripherally defined on the inner surface 14b of the outer lens 14.

The lens assembly 4 further comprises a frame 20, usually made in a single piece of polymer material, to which the outer lens 14 is applied at the front, by means of an outer double-sided tape 18, applied to the adhesion zone 14c of the inner surface 14b and to the peripheral edge of the frame 20.

Lastly, the lens assembly 4 preferably comprises an inner lens 22, made in a single piece of polymer material, having an outer surface 22a and an inner surface 22b.

The inner lens 22 is applied to the frame 20, on the side opposite the LC lens 16, for example by means of an inner double-sided tape 24, applied between the outer surface 22a of the inner lens 22 and the frame 20.

Lastly, the mask 1 comprises a photovoltaic cell 26 and an electronic circuit 28, supplied by the photovoltaic cell 26, to control the LC lens 16.

Preferably, the photovoltaic cell 26 and the electronic circuit 28 are arranged on the same support to form a single electronic board 30.

The photovoltaic cell 26 simultaneously operates as a sensor of the amount of light in the environment and as a power supply for the LC lens; in fact, the greater the amount of light which strikes the photovoltaic cell, the higher the power generated by the photovoltaic cell, the higher the power with which the LC lens is supplied and the more such an LC lens darkens.

Preferably, the electronic board 30 is supported by the frame 20, for example below a median portion 32 of the frame 20 or fixed to one of the inner 14 or outer 22 lenses.

In particular, preferably, the photovoltaic cell 26 is placed between the outer lens 14 and the inner lens 22, in a sealed frame compartment 20a formed by the frame 20, the outer lens 14 and the inner lens 22, and faces the LC lens 16.

To this end, the LC lens 16 has a recess 16d along an upper section 16c of the peripheral edge, at which the photovoltaic cell 26 is placed, so as to be struck by the light rays which only pass through the outer lens 14, which maintains the same transparency in the different use conditions; therefore, the darkening of the LC lens 16 does not affect the operation of the photovoltaic cell 26, despite the fact that such a photovoltaic cell 26 is placed sheltered in the frame compartment 20a.

The LC lens 16 preferably consists of a layer 16' with liquid crystals (hereinafter LC layer 16') and a support layer 16" made of polymer material, typically polycarbonate.

The LC layer 16' comprises liquid crystals, consisting of organic materials with large and elongated molecules, having the feature of modifying the optical properties thereof in the presence or absence of an electric field, in which dichroic particles are inserted, according to an implementation technology known as Guest-Host (GH technology).

Advantageously, the use of liquid crystals of the GH type allows to overcome a considerable drawback noted by the Applicant in the use of lenses with liquid crystals of the TN (Twisted Nematic) type, used in the currently known solutions.

Figure 5A:
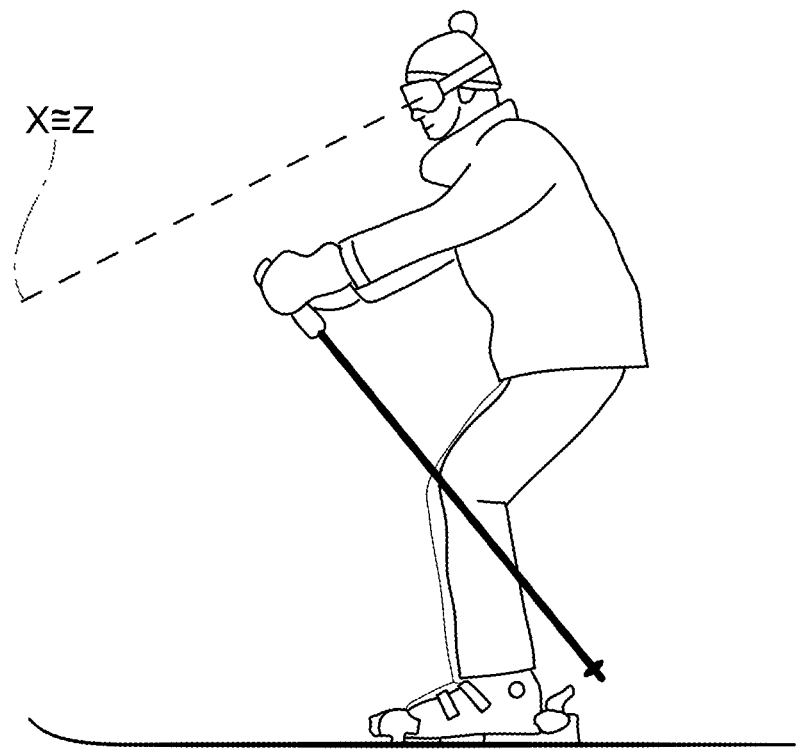
FIGS. 5a and 5b diagrammatically show two use conditions of a mask by a skier.
Figure 5B:
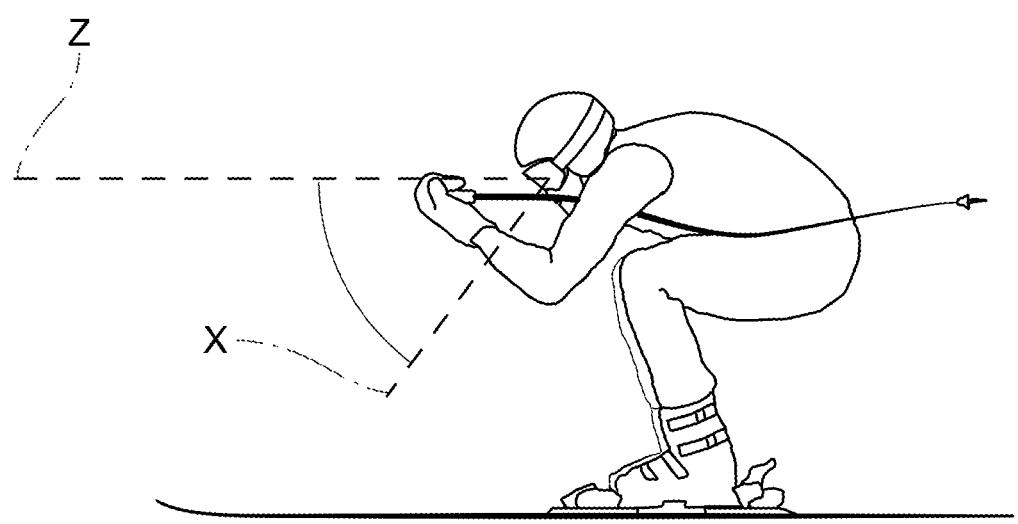

During the practice of skiing, and especially in the case of a descent, the skier typically takes two positions:

A) at low speeds (FIG. 5a), the position of the torso is almost vertical, and the gaze is focused on the ground, at a distance of a few meters; in this condition, the lens axis (X), i.e., the direction perpendicular to the lens surface, and the vision axis (Z), i.e., the axis of the eyes, are very similar, almost coinciding;

B) at high speeds (FIG. 5b), the position of the torso is almost horizontal, in contact with the thighs, and the gaze is focused much farther ahead; in this condition, the lens axis (X) is very different from the vision axis (Z).

The Applicant has found that by using masks provided with lenses with TN-type liquid crystals, in the high speed condition the vision is very obscured, even in the presence of strong environmental light.

Ultimately, the mask according to the invention, provided with a GH-type LC lens, not only allows the mask to automatically adapt to the different environmental light conditions, but also ensures excellent visibility in all the positions taken by the skier.

It is apparent that, in order to meet contingent needs, those skilled in the art may make changes to the above-described mask, all contained within the scope of protection as defined by the following claims.

What is claimed is:

1. A protective eye mask for practicing winter sports, comprising:
    an outer lens comprising an outer surface and an inner surface; and
    a liquid crystal (LC) lens comprising at least one LC layer made of guest-host (GH) type liquid crystals, wherein the LC lens is applied to the inner surface of the outer lens,
    wherein the protective eye mask comprises a photovoltaic cell for electric power supply of the LC lens,
    wherein when the photovoltaic cell is struck with a higher light intensity, the photovoltaic cell generates a higher electric power and as a result supplies the LC lens with a higher electric power, and
    wherein the LC lens of the protective eye mask comprises an upper edge provided with a recess, said photovoltaic cell being arranged at said recess.

2. The protective eye mask of claim 1, wherein the GH-type liquid crystals consist of an organic material modifying optical properties in presence or absence of an electric field, in which dichroic particles are inserted.

3. The protective eye mask of claim 1, comprising an electronic circuit, powered by the photovoltaic cell, for the electric power supply of the LC lens.

4. The protective eye mask of claim 3, wherein the photovoltaic cell and the electronic circuit are arranged on a same support to form a single electronic board.

5. The protective eye mask of claim 1, comprising an outer lens, wherein said LC lens is applied to an inner surface of the outer lens.

6. The protective eye mask of claim 5, comprising an inner lens, wherein said LC lens is arranged in front of the inner lens.

7. The protective eye mask of claim 6, comprising a frame anteriorly supporting the outer lens and posteriorly supporting the inner lens.

8. The protective eye mask of claim 7, wherein the frame, the outer lens, and the inner lens form a sealed inner compartment of the frame, said photovoltaic cell being arranged inside the sealed inner compartment.

9. The protective eye mask of claim 1, comprising a wearable support assembly, said LC lens being supported by said wearable support assembly.

10. The protective eye mask of claim 9, wherein the wearable support assembly comprises contact portions configured to adhere to a user's face to limit entry of air currents towards the user's eyes.

11. The protective eye mask of claim 1, wherein said winter sports is alpine skiing.

* * * * *